Figure 2:
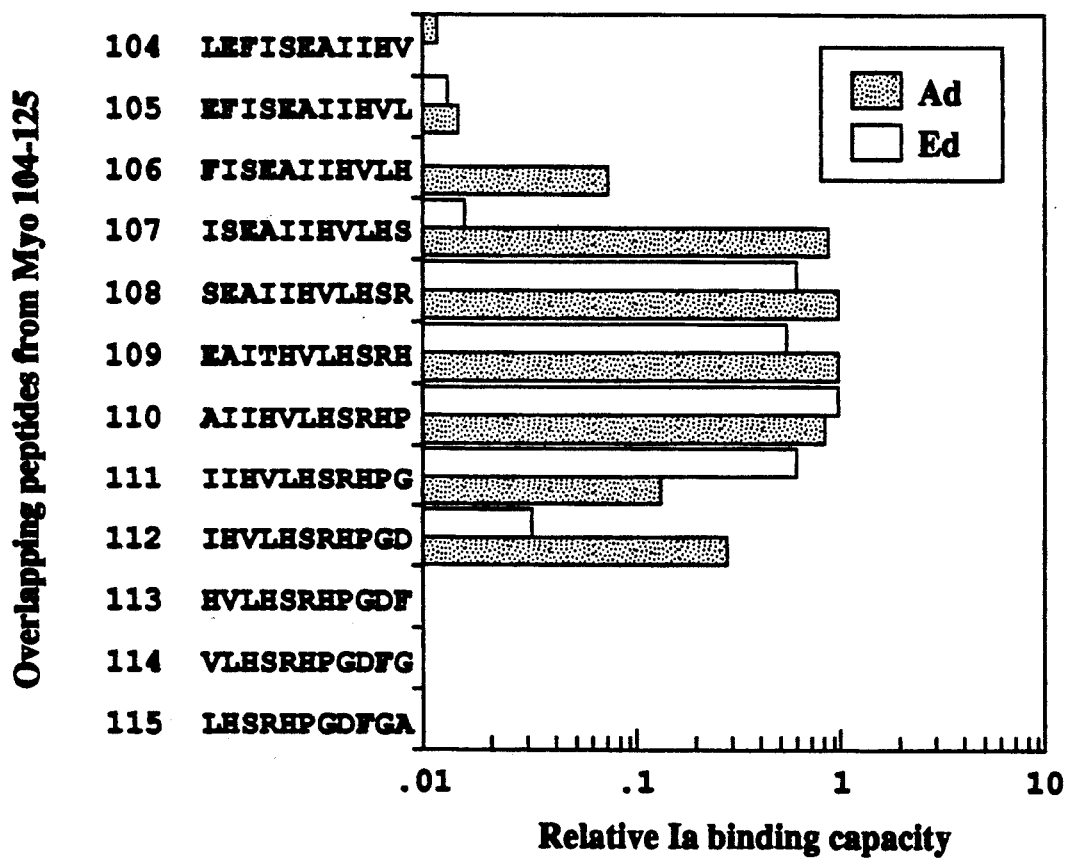

United States Patent [19]

Sette et al.

[11] Patent Number: 5,200,320

[45] Date of Patent: Apr. 6, 1993

[54] METHOD FOR IDENTIFYING USEFUL POLYPEPTIDE VACCINES

[75] Inventors: Alessandro Sette, San Diego, Calif.; Soren Buus, Copenhagen, Denmark; Howard M. Grey, San Diego, Calif.

[73] Assignee: National Jewish Center for Immunology and Respiratory Medicine, Denver, Colo.

[21] Appl. No.: 130,036

[22] Filed: Dec. 7, 1987

[51] Int. Cl.$^5$ .................. G01N 33/566; G01N 33/567
[52] U.S. Cl. .................................... 435/7.24; 435/7.8; 435/29; 436/501; 436/503
[58] Field of Search .......... 435/29, 7.24, 7.8; 436/501, 503; 424/88-92; 530/806

[56] References Cited

U.S. PATENT DOCUMENTS 4,833,092  5/1989  Geysen ................ 436/518

FOREIGN PATENT DOCUMENTS 8403564  9/1984  World Int. Prop. O. .

OTHER PUBLICATIONS

Marrack, *Science*, 235, 1311-1313, 1987.
Marx, *Science*, 235, 843-844, 1987.
Sette et al, *Nature (London)*, 328, 395-399, 1987.
Unanue et al., *Science*, 236, 551-557, 1987.
Allen et al, *Fed. Proc.*, 45 (4), p. 847, Abstr. No. 4028, 1986.
Babbit et al, *Fed. Proc.*, 45 (4), p. 847, Abstr. No. 4029, 1986.
Babbit et al, *Proc. Natl. Acad. Sci. USA*, 83, 4509-4513, 1986.
Allen et al, *Immunol. Rev.*, 98, 171-187, 1987.
Buus et al, *Science*, 235, 1353-1358, 1987.
Hackett et al, in *Immune Recognition of Protein Antigens*, Cold Spring Harbor Laboratory, 1985, pp. 48-55.
Hackett et al, *Jour. Exp. Med.*, 158, 294-302, 1983.
Livingstone et al, *Ann. Rev. Immunol.*, 5, 477-501, 1987.
Scarburough et al, *Jour. Biol. Chem.*, 261, 12960-12964, 1986.

*Primary Examiner*—David Saunders
*Attorney, Agent, or Firm*—Felfe & Lynch

[57] ABSTRACT

A method of identifying potential polypeptide vaccines to an agent, such as viruses, bacteria, and parasites. A critical binding segment of a first polypeptide known to bind to a first MHC type, is ascertained. The effect of replacing each of the amino acids in the critical segment, upon binding of that segment to the first MHC type, is evaluated. Following this, a protein produced by the agent is scanned for at least one trial amino acid sequence which the foregoing evaluation indicates will be a good binder to the first MHC type. When a potentially good binding sequence is found, a polypeptide containing such sequence can be evaluated as a synthetic vaccine.

2 Claims, 3 Drawing Sheets

```
10   HOME : PRINT "": PRINT "JUST A MOMENT PLEASE"
20   DIM VA(10,25),D$(50)
30   FOR I = 1 TO 7
40   FOR J = 1 TO 25
45   READ VA(I,J)
50   NEXT J
60   NEXT I
65   FOR I = 1 TO 42: READ D$(I): NEXT I
70   PRINT "MASTER SEQ. =VHAAHAE"
80   INPUT "INPUT SEQUENCE # ";SN:B$ = D$(SN):LB = LEN (B$)
90   FOR J = 0 TO LB - 7:PR = 1
150  FOR I = 1 TO 7
160  A = ASC ( MID$ (B$,I + J,1)) - 64
170  VA = VA(I,A):PR = PR * VA
190  NEXT I
200  PRINT MID$ (B$,J + 1,7),PR: NEXT J: INPUT Q$: GOTO 80
210  DATA 3,0,2,1,1,1,1,1,3,0,1,3,2,1,0,2,1,1,2,2,0,4,1,0,1
220  DATA 2,0,2,2,2,1,2,4,2,0,3,2,1,2,0,1,2,3,3,3,0,2,1,0,2
230  DATA 4,0,2,2,2,2,3,2,3,0,1,3,2,2,0,2,3,2,3,3,0,3,2,0,3
240  DATA 4,0,2,2,2,2,2,2,3,0,2,3,2,2,0,3,2,3,3,3,0,3,2,0,3
250  DATA 3,0,3,2,2,2,1,4,3,0,3,3,2,1,0,1,3,3,3,3,0,3,2,0,3
260  DATA 4,0,2,1,1,1,2,1,2,0,1,2,2,1,0,2,1,1,3,3,0,2,1,0,1
270  DATA 3,0,2,2,4,2,2,3,2,0,3,2,2,3,0,2,3,3,3,3,0,3,2,0,3
505  REM "OVA323-339"
510  DATA "ISQAVHAAHAEINEAGR"
515  REM "HA130-142"
520  DATA "HNTNGVTAACSHE"
525  REM "L REPR12-26"
530  DATA "LEDARRLKAIYEKK"
535  REM "HEL46-61"
540  DATA "NTDGSTDYGILQINSR"
545  REM "HEL74-86"
550  DATA "NLCNIPCSALLSS"
555  REM "HEL81-96"
560  DATA "SALLSSDITASVNCAK"
565  REM "HA111-122"
570  DATA "FERFEIFPKESS"
575  REM "MYO132-153"
580  DATA "NKALELFRKDIAAKYKELGYQG"
580  DATA "NKALELPRKDIAAKYKELGYQG"
585  REM "HSVB-23"
590  DATA "SLKMADPNRFGKDLP"
595  REM "PCYT88-104"
600  DATA "KAERADLIAYLKQATAK"
605  REM "MCYT88-103"
610  DATA "ANERADLIAYLKQATK"
615  REM "MYO106-118"
620  DATA "YFISEAIIHVLHSR"
625  REM "VIVAX TRI."
630  DATA "NANPNANPNANP"
635  REM "FLUNUCL 366-379"
640  DATA "ASNENMDAMESSTL"
645  REM "FALCDIM"
650  DATA "DGQPAGDRADGQPAGDRA"
```

FIG. 1A

FIG. 1B

```
655  REM  "NASE1-20"
660  DATA "ATSTKKLHKEPATLIKAIDG"
665  REM  "NASE11-30"
670  DATA "PATLIKAIDGDTVKLMYKGQ"
675  REM  "NASE21-40"
680  DATA "DTVKLMYKGQPMTPRLLLVD"
685  REM  "NASE31-40"
690  DATA "PMTPRLLLVDTPETKHPKKG"
695  REM  "NASE41-60"
700  DATA "TPETKHPKKGVEKYGPEASA"
705  REM  "NASE51-70"
710  DATA "VEKYGPEASAFTKKMVENAK"
715  REM  "NASE61-80"
720  DATA "FTKKMVENAKKIEVEFDKGQ"
725  REM  "NASE71-90"
730  DATA "KIEVEFDKGQRTDKYGRGLA"
735  REM  "NASE81-100"
740  DATA "RTDKYGRGLAYIRADFKMVN"
745  REM  "NASE91-110"
750  DATA "VIRADFKMVNEALVRQGLAK"
755  REM  "NASE 101-120"
760  DATA "EALVRQGLAKVAYVYKPNNT"
765  REM  "NASE111-130"
770  DATA "VAYVYKPNNTHEQHLRKSEA"
775  REM  "NASE121-140"
780  DATA "HEQHLRKSEAQAKKEKLNIW"
785  REM  "NASE131-149"
790  DATA "QAKKEKLNIWSEDNADSGQ"
795  REM  "HSV-D-196-210"
800  DATA    "IPPSACLSPQAYQQG"
805  REM     "HSVD245-260
810  DATA     "APYTSTLLPPELSETP"
815  REM    " HSVD204 - 219 "
820  DATA  "PQAYQQGVTVDSIGML"
825  REM    "SWMYO63-78"
830  DATA "KHGVTALTALGAILKK"
835  REM  "HCYTC11-27"
840  DATA   "VQKCAQCHTVEKGGKHK"
845  REM  "OVA108-7"
850  DATA "SSAESLKISQA"
855  REM  "JF39"
860  DATA "AHRVQLGPRSLQVLLIP"
865  REM  "ED122-ALFA6.20"
870  DATA "ADHVGSYGITVYQSP"
875  REM  "KM119"
880  DATA "QPEILERRTRAEVDTACR"
885  REM  "DYNODRFHIN"
890  DATA "YGGPLRRIRPKLK"
895  REM  "LYSOZYME34-45"
900  DATA "FESNFNTQATR"
905  REM  "BRAD POT B"
910  DATA "EGLPPRPKIPP"
915  REM  "LYSO105-120"
920  DATA "MNAWVAWRNRCKGTDV"
```

METHOD FOR IDENTIFYING USEFUL POLYPEPTIDE VACCINES

FIELD OF THE INVENTION

This invention relates to a method for identifying polypeptide sequences which may serve as a vaccine for an agent, such as a virus.

TECHNOLOGY REVIEW

Cytotoxic and Helper T-cells play a fairly well understood role in combating infectious agents, such as bacteria, viruses, and parasites. In order to immunize an animal (including humans) against a particular infectious agent, it is necessary to activate T-cells specific for a protein (antigen) derived from the agent. It has previously been suggested that the final step in this activation of T helper cells is the creation of a trimolecular complex consisting of major histocompatibility complex (MHC) II molecules (Ia molecules), 'processed' antigenic protein (both on antigen presenting cells -APC), and the T-cell receptor. See, for example, Heber-Katz, et al.; J. Molec Cell. Immun.; Vol. 1, p. 3–14 (1983). As a necessary step in the formation of the foregoing complex, the processed antigen must bind to Ia molecules of the APC of the individual animal to be immunized.

For a number of reasons, synthetic peptides derived from infectious agents may be useful as vaccines. Preferably, such a polypeptide should have an amino acid sequence which will result in an immunogenic response in as many individuals of a species as possible. This requires selecting from a protein derived from the agent a polypeptide which will bind to all of the major alleles of class II MHC found in a species. Such a task become formidable given the variations in amino acid sequence (polymorphism) within the class II MHC, and the extremely large number of peptide sequences which can be chosen from a selected protein produced by the agent.

SUMMARY OF THE INVENTION

The present invention then, provides a method which can preferably be used to identify potential polypeptide vaccines to an agent, that is, polypeptides which potentially function as vaccines, while screeing out those unlikely to so function. The method has particular application in identifying potential polypeptide vaccines for a number of individuals expressing different MHC class II types, although it can also be used to identify potential polypeptide vaccines for one or more individuals expressing the same MHC class II type. In a broader embodiment, the method can be used to identify polypeptides which will bind to any target polypeptide (the latter being longer than the former).

For simplicity in the following discussion, "MHC type" will refer to a different allele of the class II MHC (that is, having a different amino acid sequence), a "sequence" of a polypeptide or a protein will be understood as referring to the amino acid sequence thereof, while the "length" of a polypeptide or protein will be understood as referring to the number of amino acids thereof.

The present method of identifying potential polypeptide vaccines then, basically comprises ascertaining a critical binding segment of a first polypeptide that binds well to a first type of MHC. By a "critical binding segment" is meant a sequence of the polypeptide such that removal of either of the outermost (i.e., peripheral or "flanking") amino acids, will result in a substantial reduction of binding strength to that MHC type (typically a reduction of one-half or more). The effect on the foregoing binding strength, of replacement of at least some (and preferably all) of the amino acids thereof, by other (and preferably all possible) amino acids is then evaluated. Preferably, the aminoacids are individually replaced, that is, only one amino acid is replaced by another amino acid at a time, and the resulting effect on binding strength evaluated.

The evaluation of the effect on binding strength, that results from the replacement of the amino acids of the critical binding segment, is ideally accomplished by actually testing of the binding of the resulting polypeptide to the first MHC type. However, if actual binding data of such resulting polypeptides is unavailable, it is possible to evaluate the effect on binding strength of amino acid replacements, by estimating techniques as will be described below.

The protein derived from the agent can then be reviewed for at least one sequence which the above evaluation indicates should be a good binder.

In a preferred embodiment of the present invention, a designation is assigned to each amino acid substitution at each position of the critical segment, corresponding to its effect on the binding of the corresponding substituted polypeptide to the first MHC. Typically, the designation will be numerical, with higher numbers indicating less adverse effect on binding strength (or even a positive effect on binding strength). A function product of the designations of the amino acid types of at least one trial sequence of a protein produced by the agent, is then determined. By a "function product" is meant performing a function on the designations of each amino acid type, which results in a product corresponding to the relative expected binding strength of that trial sequence in relation to other sequences (for example, the critical binding segment). For example, such a function may be a multiplication of numerical designations assigned to each amino acid type found in the trial sequence (which numerical designations may also take into account the location of the amino acid in the sequence). Thus, the function product from the trial sequence will provide a measure of the expected binding of that sequence to the first MHC type. However, the function need not be multiplication, and thus the "product" thereof is not necessarily a multiplicative product.

In a typical situation, the function product of the amino acid types of a plurality of trial sequences, will be ascertained, each according to the method already described. Preferably the method additionally comprises actually testing a polypeptide containing at least a trial sequence, and which has a function product indicating sufficiently high expected binding, for either binding to the first polypeptide or immunogenic activity.

Whether any particular function product indicates sufficiently high binding, can be evaluated by measuring the binding strength of a test series of polypeptides to the first MHC type. To obtain meaningful results, each of the polypeptides of the test series should be at least equal in length to the critical binding segment, and contain only sequences differing therefrom by at least two amino acids. A best function product of each polypeptide of the test series is determined in a manner described below, and the actual measured binding strengths compared with the best function products. The numerical designation of some or all of the amino acid substitutions can at this point be altered, in order to maximize the correlation between the best function products of the test series and their actual measured binding strengths. A threshold function product can then be established which indicates a threshold of sufficient binding strength to the first MHC type. If the numerical designations are used for amino acid types in the manner already described, then a number equal to or above the threshold function product will indicate sufficient binding strength. The value which will be chosen as the threshold function product will depend upon a compromise between certainty of including all trial sequences which will actually bind, while at the same time avoiding inclusion of trial sequences which will not actually bind.

DRAWINGS

Embodiments of the invention will now be described with reference to the single Figure, which illustrates a method of the present invention for ascertaining a critical binding segment of a polypeptide to two MHC types.

DETAILED DESCRIPTION OF EMBODIMENTS OF THE INVENTION

In the descriptions which follow, the standard single-letter abbreviations for amino acids listed below in Table 1 (attached) will be used.

TABLE 1

| Abbreviations for amino acids | | |
|---|---|---|
| Amino Acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | O |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionina | Met | M |
| Phenylalanine | Phe | F |
| Proline | Pro | P |
| Serine | Ser | S |

TABLE 1-continued

| Abbreviations for amino acids | | |
|---|---|---|
| Amino Acid | Three-letter abbreviation | One-letter symbol |
| Threonine | Thr | T |
| Tryptophan | Trp | W |
| Tyrosine | Tyr | Y |
| Valine | Val | V |

The following examples will illustrate the method of the present invention. First, a critical binding segment of a first polypeptide that binds to a first type of MHC, was ascertained. In particular, the critical binding segment of the immunogenic polypeptide Ova 323–339 (derived from chicken ovalbumin), for the MHC type I-A from the d strain of mouse (i.e. $IA^d$), was ascertained. This was accomplished by the method described in Sette, et al, Nature, Vol. 238 No. 6129, pp. 395–399, Jul. 30, 1987, the entirety of which is incorporated herein by reference. As described in the foregoing paper, two series of polypeptides were synthesized, each series containing sequences corresponding to progressive truncations from a corresponding end of the first polypeptide (Ova323-339). For convenience, Table I of that paper illustrating the foregoing procedure, is attached as Table 2.

TABLE 2

Effect of N- and C-terminal truncations of Ova 323-339 on $I\text{-}A^d$ binding capacity

| Ova peptide | Sequence | | | | | | | | | | | | | | | | | Relative $I\text{-}A^d$ binding capacity* |
|---|---|---|---|---|---|---|---|---|---|---|---|---|---|---|---|---|---|---|
| | C-terminal truncations | | | | | | | | | | | | | | | | | |
| 323–339 | I | S | Q | A | V | H | A | A | H | A | E | I | N | E | A | O | R | |
| 323–336 | — | — | — | — | — | — | — | — | — | — | — | — | — | E | | | | 1.1 |
| 323–335 | — | — | — | — | — | — | — | — | — | — | — | — | N | | | | | 1.0 |
| 323–333 | — | — | — | — | — | — | — | — | — | — | E | | | | | | | 0.6 |
| 323–332 | — | — | — | — | — | — | — | — | — | A | | | | | | | | 0.2 |
| 323–331 | — | — | — | — | — | — | — | — | H | | | | | | | | | <0.005 |
| | N—terminal truncations | | | | | | | | | | | | | | | | | |
| 325–339 | | | Q | — | — | — | — | — | — | — | — | — | — | — | — | — | — | 1.1 |
| 326–339 | | | | A | — | — | — | — | — | — | — | — | — | — | — | — | — | 0.5 |
| 327–339 | | | | | V | — | — | — | — | — | — | — | — | — | — | — | — | 0.3 |
| 328–339 | | | | | | H | — | — | — | — | — | — | — | — | — | — | — | 0.014 |
| 329–339 | | | | | | | A | — | — | — | — | — | — | — | — | — | — | <0.005 |

Peptide antigens were synthesized, cleaved and HPLC purified, $I\text{-}A^d$ molecules were obtained by affinity purification of lysates of B-cell lymphoma A20 with the monoclonal anti-$I\text{-}A^d$ antibody MKD6 (Buus et al, Proc. Natn. Acad. Sci. U.S.A., Vol. 83, 3968–3971 (1986)). The $I\text{-}A^d$ interacting capacity of each peptide is expressed as the amount of unlabelled Ova 323–339 divided by the amount of truncated peptide needed to inhibit the binding of $^{125}$I-radiolabel led Ova 323–339 to $I\text{-}A^d$ by 50% as measured by a gel filtration method of Buus et al, Cell, Vol. 47, pp. 1071–1077 (1986). The data represent the averages of 2–4 experiments.

As described by Sette, et al, supra, the critical binding segment (that is the sequence which includes amino acid 'flanks', the removal of either of which results in a marked decrease in the binding strength) for the first polypeptide, is VHAAHA. The effect on binding strength to $IA^d$ of replacing each of the amino acids of the critical binding sequence in turn, with each of the other 20 amino acids, was then evaluated. This was accomplished in two ways. First, each of the amino acids of the critical binding segment was individually replaced by some of the 20 amino acids, and the binding strength of each resulting sequence to the OVA323-339 experimentally determined. Each replacement for each amino acid in the critical binding segment, which was actually made and the binding strength experimentally determined, is indicated by an "X" in Table 3, which is attached.

TABLE 3

| | $0_A$ | $1_V$ | $2_H$ | $3_A$ | $4_A$ | $5_H$ | $6_A$ | $7_E$ | $8_I$ |
|---|---|---|---|---|---|---|---|---|---|
| A | X | X | X | X | X | X | X | X | |

TABLE 3-continued

| | $0_A$ | $1_V$ | $2_H$ | $3_A$ | $4_A$ | $5_H$ | $6_A$ | $7_E$ | $8_I$ |
|---|---|---|---|---|---|---|---|---|---|
| C | | | | | | | | | |
| D | | X | | | | | | X | X |
| E | | | X | | | X | | X | |
| F | | | | | | | | | |
| G | X | X | X | X | X | X | X | X | X |
| H | | | X | | | X | | | |
| I | | X | | | | | | X | X |
| K | | | X | | | X | | | |
| L | | X | X | | | X | | | X |
| M | | | | | | | | | |
| N | | | X | | | X | | | |
| P | X | X | X | X | X | X | X | X | X |
| Q | | | X | | | X | | X | |
| R | X | X | X | X | X | X | X | X | X |
| S | X | X | | X | X | X | X | | |
| T | | X | X | | | | | | X |
| V | X | X | X | X | X | X | X | | X |
| W | | | | | | | | | |
| Y | X | | | X | X | | X | X | |

In Table 3, the critical binding segment (plus additional amino acids on either end thereof) is listed across the top of the table, while the 20 possible amino acid types are listed down the left-hand side thereof. The amino acid which is the same as the amino acid "substituted" at that position, is also marked with an "X" for completeness of the Table. Thus, for example, six analogs of the sequence shown at the top of the Table III were prepared, in which the A at position 0 was replaced in turn by G, P, R, S, V, and Y, and their binding to $IA^d$ experimentally determined quantitatively. Likewise, another nine analogs were prepared, in which the "V" at position 2 was replaced in turn by each of the polypeptides listed on the left-hand column in Table III on the lines of which an "X" is indicated underneath the position at 2 V, and the binding to $IA^d$ experimentally determined quantitatively. This procedure was repeated for the remainder of the amino acids of the sequence at the top of Table 3.

The effect which the substitutions indicated by an "X" in Table III, had on the binding strength of the critical binding segment listed at the top of attached Table 4, was quantitatively calculated, and a numerical designation assigned to the substituting amino acid based upon the degree of that effect. The foregoing assigned numerical designations for each "X" position indicated in Table 3, is listed at corresponding positions in Table 4. The quantitative evaluations of the binding strength were made using a competition assay as described in Sette, et al, supra, and the numerals assigned according to the decrease in the binding activity as follows:

4 = identity (e.g. V "replacing" a V at that position)
3 = no substantial change in binding strength
2 = moderate change in binding strength (i.e. binding capacity as ascertained by the method described in connection with Table 2 above, decreased by a factor of approximately 2 to 10)
1 = a large change in binding strength (binding capacity as determined by the method in association with Table 2 above, decreased by approximately 10 to 100).

When numerals are indicated in Table 4, and no corresponding "X" appears in Table 3, this means that the numerical evaluations for that amino acid type was performed on a theoretical basis. This theoretical basis is somewhat arbitrary and it takes into account a number of factors. First, if the structures of a replacing and replaced amino acid are very similar, then a value of 3 is assigned to the replacing amino acid.

TABLE 4

| | $1_V$ | $2_H$ | $3_A$ | $4_A$ | $5_H$ | $6_A$ | $7_E$ |
|---|---|---|---|---|---|---|---|
| A | 3 | 2 | 4 | 4 | 3 | 4 | 3 |
| C | 2 | 2 | 2 | 2 | 3 | 2 | 2 |
| D | 1 | 2 | 2 | 2 | 2 | 1 | 2 |
| E | 1 | 2 | 2 | 2 | 2 | 1 | 4 |
| F | 1 | 1 | 2 | 2 | 2 | 1 | 2 |
| G | 1 | 2 | 3 | 2 | 1 | 2 | 2 |
| H | 1 | 4 | 2 | 2 | 4 | 1 | 3 |
| I | 3 | 2 | 3 | 3 | 3 | 2 | 2 |
| K | 1 | 3 | 1 | 2 | 3 | 1 | 3 |
| L | 3 | 2 | 3 | 3 | 3 | 2 | 2 |
| M | 2 | 1 | 2 | 2 | 2 | 2 | 2 |
| N | 1 | 2 | 2 | 2 | 1 | 1 | 3 |
| P | 2 | 1 | 2 | 3 | 1 | 2 | 2 |
| Q | 1 | 2 | 3 | 2 | 3 | 1 | 3 |
| R | 1 | 3 | 2 | 3 | 3 | 1 | 3 |
| S | 2 | 3 | 3 | 3 | 3 | 3 | 3 |
| T | 2 | 3 | 3 | 3 | 3 | 3 | 3 |
| V | 4 | 2 | 3 | 3 | 3 | 2 | 3 |
| W | 1 | 1 | 2 | 2 | 1 | 1 | 2 |
| Y | 1 | 2 | 3 | 3 | 3 | 1 | 3 |

Another means for obtaining a qualitative evaluation or untested substitutions, is by reference to Dayhoff's scoring system for similarities of polypeptides, such as is illustrated by Russell F. Doolittle in "Urfs and Orfs—a Primer on How to Analyze Amino Acid Sequences"; University Science Book (1986), Mill Valley, Calif., U.S.A., Page 114, Table 1, incorporated herein by reference. In such a scoring system, higher numbers indicate a higher degree of amino acid similarity, and thus, in the above scoring system when one is replaced with another, the replacing amino acid should be given a high score (for example, a "3").

However, the Dayhoff similarity scores should be tempered with the knowledge from the above experimentally ascertained bindings, that different positions of the critical binding sequence, exhibit different sensitivities to replacement. As a measure of this sensitivity, a P/T (Permissible/Total) ratio was generated for each position in the critical binding segment of Ova 323-339, as given in attached Table 5. To obtain this ratio, all permitted and non-permitted substitutions (those which did not, and did, respectively, severely affect binding as determined in the binding experiments performed to generate Tables 3 and 4) for each position of that critical binding segment, were listed in the second and third columns of Table 5. The total frequency with which all members of each group (a group being those within parentheses in Table 5), occurs in nature was evaluated as a fraction indicated in colums two and three, using frequencies of occurrence of amino acids in nature from the Table XI, p. 55 of A. Doolittle, supra. The total frequency of occurence (appearing under "Total" column of attached Table 5) was then calculated, followed by calculation of a P/T ratio.

Thus Dayhoff scores would be lowered where a lower P/T ratio was indicated by Table 5. For example, using the above weighted Dayhoff scores, the "F" replacing the "A" at position 3 in column 1 of Table 4, was assigned a designation of 2, because position 3 is permissive while the same substitution at position 5 was given a 1 because that position is less permissive.

TABLE 5

| | FREQUENCIES | | | | |
|---|---|---|---|---|---|
| Ova A.A. | Permitted Substitutions | Non-Permitted Substitutions | | Total | P/T |
| Q | 0.335 (NESYLQ) | — | 6 | 0.335 | 1.00 |
| A | 0.420 (PGSVRYA) | — | 7 | 0.420 | 1.00 |
| V | 0.347 (VILTA) | 0.192 (DRSGP) | 10 | 0.539 | 0.64 |
| H | 0.326 (HTRKQL) | 0.229 (ENPG) | 10 | 0.555 | 0.59 |
| A | 0.367 (AGSYRY) | 0.052 (P) | 7 | 0.419 | 0.88 |
| A | 0.352 (ASVRYP) | 0.072 (G) | 7 | 0.424 | 0.83 |
| H | 0.417 (RQKELHSC) | 0.167 (PNG) | 11 | 0.584 | 0.71 |
| A | 0.264 (ASVP) | 0.156 (GRY) | 7 | 0.420 | 0.63 |
| E | 0.365 (DQRYEGP) | 0.053 (I) | 8 | 0.418 | 0.87 |
| I | 0.477 (PLVTRDIG) | — | 8 | 0.497 | 1.00 |
| N | 0.282 (DQTYIN) | — | 6 | 0.282 | 1.00 |

Following the generation of the designations in Table 4, a best function product of each polypeptide of a test series of polypeptide listed in attached Tables 6 and 7, was determined. That is, the function product (multiplication product) of the designations of the amino acid types (the numerical values assigned in Table 4) were determined for each sequence of each polypeptide listed in those tables, which sequence is equal in length to the critical binding segment (for those calculations, taken as the seven amino acid sequence VHAAHAE). For example, taking the Ha 130-142 polypeptide listed in Table 7, the function product of the first seven amino acid sequence (HNTNGVT) would be determined using assignments of each polypeptide at its position, as listed in Table 4. The function product for the next seven amino acid sequence (NTNGIVTA) would then be determined using the values from Table 4. Likewise, the function product of the remainder of the seven sequences of that polypeptide would also be determined. The function product of one of the seven sequences would be selected, which indicates the sequence expected to bind more strongly to the first MHC type (IA$^d$). In particular, under the above numerical designation system and with the function being multiplication, the multiplication product of the one sequence, out of the seven, seven amino acid sequences of the polypeptide Ha 130-142, which is the highest number, would be selected as the best function product of that polypeptide. That number is listed as the "score" 5184, in Table 7.

TABLE 6

| POOR BINDERS | | |
|---|---|---|
| Polypeptide | Sequence | Numerical Score |
| Nase 51 | | 640 |
| Nase 131 | | 320 |
| KM 119 | | |
| Lys 34-45 | | 324 |
| Nase 21 | | 324 |
| Nase 31 | | 296 |
| Nase 41 | | 576 |
| Nase 71 | | 576 |
| Nase 111 | | 296 |
| Nase 121 | | 570 |
| Ha 111-120 | | 216 |
| Myo 132-153 | | 648 |
| mcyt | | 1296 |
| Falc Dim | | 144 |
| Nucl Prot GU3 | | 576 |
| Dynorfin | | 216 |
| Bred pot B | | 288 |
| Lys 105-120 | | 768 |
| HSV 8-23 | | 864 |
| Hyo gliding 111.1 | YLEFISEAICH | 1296 |
| KM 118 | QPEILERTRACVDTACR | 1728 |
| C 143 | YPKPEYLQCVK | 648 |

TABLE 6-continued

| POOR BINDERS | | |
|---|---|---|
| Polypeptide | Sequence | Numerical Score |
| Ed 123 alpha 50-64 | PEFAQLRRFEPQGGL | 576 |
| 136.1 | SSSANLSGISS | 864 |
| C 151 | HIATNAVLFFGR | 864 |

TABLE 7

| GOOD BINDERS (0-50M) | | | |
|---|---|---|---|
| NAME/ ORIGIN | SEQUENCE | BINDING (M) | SCORE |
| Ova 323-339 | ISQAVHAAHAEINEAGR | 10 | 16384 |
| Ha 130-142 | HNTNGUTAACSHE | 9 | 5184 |
| Myo 106-118 | | 20 | 3888 |
| Nase 101-120 | | 13 | 2592 |
| Myo 63-78 | | 9 | 3456 |
| Ova Site II | SAESLKISQAV | 5 | 2916 |
| Ed 122 alpha 6-20 | | 3 | 1458 |
| JF 39 | | 25 | 864 |
| HSVD 245-260 | APYTSTLLAPELSETP | 22/2 | 648 |
| HSVgD 196-210 | | 56/2 | 1296 |

TABLE 8

| | | | Total |
|---|---|---|---|
| | Greater than 1000 | Less than 1000 | |
| Good Binders | 8 | 2 | 10 |
| Non-Binders | 5 | 21 | 26 |
| | Greater than 2000 | Less than 2000 | |
| Good Binders | 6 | 4 | 10 |
| Non-Binders | 0 | 22 | 22 |

The listing of a computer program used to determine the best function products of the polypeptide listed in Tables 6 and 7, is also attached as an "Appendix". The foregoing listing is in BASIC source code.

The value of "binding" listed in Tables 6 and 7, is in micromolar concentration of the indicated polypeptide. The assay used was the same as that in Sette et al, supra, for quatitative estimation of Ia peptide interaction. Polypeptides which had bindings less than 50 micromolar, were considered to be good binders and listed in Table 7. Those polypeptides with bindings greater than 3000 micromolar, were considered to be negative Ia binders and listed Table 6.

The measured binding strengths of each polypeptide of the test series In Tables 6 and 7, can then be compared with their respective best function products listed in those Tables. By such a comparison, a threshold function product can be selected, which indicates a threshold of sufficient binding strength to the first MHC type (IA$^d$).

The selection of the threshold function product is based upon a consideration of inclusion of maximum number of good binders on one side of the threshold limit, along with inclusion of minimum number of non- or poor binders. For example, threshold function products which might be selected might include values such as 1000 or 2000. The number of good binders and non-binders which are covered by selection of either of the foregoing two threshold function products, is indicated in attached Table 7.

Thus, a threshold function product of 2000 may be chosen, if it was desired to include most polypeptide sequences exhibiting a good binding while eliminating all polypeptide sequences being non-binding, which have best function products above 2000. Alternatively, a threshold function product of 1000 could be chosen if it was desired to include more good binders, while at the same time also including approximately 20% of the non-binders.

It should, of course, be borne in mind that the foregoing numbers are arbitrary and that other numbers or designations can be assigned to each replacing amino acid in Table 4. In addition, other functions operating thereon, can also be selected. For example, each assigned number could be raised to a given exponential power.

It should, of course, be borne in mind that ascertaining binding strength of a polypeptide, does not necessarily mean T-cell recognition in a three-way complex of the type described above. In particular, as pointed out in Sette et al., supra, T-cell recognition is much less permissive than MHC recognition. Thus, the fact that a polypeptide has a good binding to an MHC type, does not necessarily insure immunogenicity. However, as one would expect, when the binding strength of a polypeptide to an MHC types of an individual animal is poor, little or no immunogenic response would result. However, if a polypeptide is a good binder, as ascertained by the above method, then immunogenicity would be expected to be a possibility. These expectations are borne out by the results indicated in attached Table 9. Binding to a class II MHC type $IA^d$ and $IE^d$ (d strain of mouse) was evaluated using the same assay technique as used to evaluate the binding for the polypeptides in Tables 6 and 7 above.

TABLE 9

Relation between $Ia^d$ binding capacity and immunogenicity of peptides derived from staph. nuclease

| N-ase Peptide | Binding $A^d$ | $E^d$ | Immunogenicity |
|---|---|---|---|
| 1–20 | 3+ | — | 2+ |
| 11–30 | 2+ | — | — |
| 21–40 | — | — | — |
| 31–50 | — | — | — |
| 41–60 | — | — | — |
| 51–70 | — | — | — |
| 61–80 | 2+ | — | 2+ |
| 71–90 | — | — | — |
| 81–100 | 2+ | — | — |
| 91–110 | 2+ | — | — |
| 101–120 | 4+ | 2+ | 2+ |
| 111–130 | — | 2+ | 1+ |
| 121–140 | — | — | — |
| 131–149 | — | — | — |

The following assignments were made for binding in Table 9:

4+ = 0 to 50 micromolar range of peptide required
3+ = 50 to 100 micromolar range
2+ = 100 to 500 micromolar range
1+ = 500 to 1000 micromolar range
Negative = Greater than 1000 micromolars.

Immunogenicity was determined by a T-cell proliferation response, in which T-cells were exposed to the antigenic polypeptide, and their response measured by their capacity to incorporate tritiated thymidine. A "—" (negative value) was assigned under "Immunogenicity" if the counts per minute (CPM) was less than 10,000, a +1 assigned if the CPM was between 10,000 and 40,000, and a +2 assigned if the CPM was greater than 40,000.

The results from Table 9 are summarized in attached Table 10 in terms of the number of peptides exhibiting a binding ("+") or a non-binding ("—"), and their corresponding immunogenicity, a "+" being positive immunogenicity, and a "—" being negative immunogenicity. All of the polypeptide from Table 9 which exhibit a "—" (non-binding), also exhibit negative immunogenicity. There were no polypeptide from Table 9 which exhibited negative binding and which also exhibited positive immunogenicity. However, three polypeptides in Table 9 which exhibited positive binding, exhibited negative immunogenicity. Table 10 also indicates that two polypeptides from Table 9 (1–20 and 101–120), both exhibited positive binding to IA from d and k strains of mice. Likewise, the same foregoing two polypeptides also exhibited positive immunogenicity with T-cells from those strain of mice.

TABLE 10

Summary of binding and immunogenicity of staph. nuclease peptides

| No. of Peptides | Binding | Immunogenicity |
|---|---|---|
| 7 | — | — |
| 0 | — | + |
| 4 | + | + |
| 3 | + | — |
| 2 | + (d + k) | + (d + k) |

It will be seen from the above then, that when a polypeptide is indicated as being a good binder to an MHC type, this does not necessarily mean that it will cause an immunogenic response. However, if the above method ascertains that a polypeptide is not a good binder, then it generally will not provide any immunogenic response. Thus, the selection of a polypeptide having suitable sequences, is considerably simplified since the present method provides a good indication of those polypeptides which will not work, as well as those which may work.

Of course, it should be borne in mind that in view of the more stringent recognition requirement of T-cells versus MHC, and in particular since T-cells apparently tend to recognize only amino acid sequences of greater than about 8 in length, a polypeptide should be chosen as a candidate for evaluating immunogenic response, which contains both a sequence which the above method indicates will be a good binder to MHC, as well as additional flanking sequences determined from the antigenic protein of the agent, such that the total polypeptide length is about 15 to 20 amino acids.

It will be seen from the above that the effectiveness of a polypeptide as a vaccine could be increased if it is capable of binding strongly to different MHC types from the same individual. Furthermore, the vaccine spectrum (that percentage of the population of a species in which it will be an effective immunogen) will likely to he increased if the polypeptide will bind with different MHC alleles from different individuals. In particular, in the case of humans, the major types of MHC are described in "Immunological Reviews," Vols. 84 and 85 (1985), and Goran Moller, Editor; "Molecular Genetics of Class I and Class II MHC Antigens"—Munksgaard-Copenhagen, which are incorporated herein by reference, and which broadly describes the molecular genetics of class I and class II MHC antigens. Thus, the method described can be used for multiple MHC types to ascertain trial sequences which are potentially capable of binding multiple MHC types from either the same or different individuals.

As an example of a situation in which the same critical binding sequence can bind two different MHC types, and to determine the critical binding segment of a polypeptide to two MHC types, and to illustrate structural similarities between $IA^d$ binding peptides from unrelated proteins, a series of overlapping undecapeptides were synthesized spanning through residues 103-125 of sperm wale myoglobin ($M_{yo}$ 103-125). This peptide region was selected as it had been shown to be antigenic for both $IA^d$ and $IE^d$ restricted T-cells, and therefore provided the opportunity of defining the $IA^d$ and $IE^d$ interacting regions within a single peptide. As noted in the Figure, myoglobin 103-123 contains the sequence IHVLHS, which is quite similar to the Ova 327-332 VHAAHA sequence. The critical-binding segment of $M_{yo}$ 103 to 125 to $IA^d$, was ascertained by measuring the relative binding of a number of overlapping polypeptide on the left-hand column of the Figure, to mouse $IA^d$. The foregoing polypeptides can be regarded as two series, the polypeptide of each series having sequences homologous to respective end truncation products of $M_{yo}$ 103-125.

The relative binding strength in each case was ascertained in the same manner as described in connection with the bindings evaluated in Table 2. The $IA^d$ binding profile of the overlapping peptides that encompass the residues 103-123 of myoglobin is shown in the Figure. From these data it can be concluded that the C-terminal limit of the region containing this $IA^d$ binding site is centered around residue $H_{116}$ and $S_{117}$, since removal of $S_{117}$ resulted in a 10-fold decrease in binding activity, while further removal of $H_{116}$ completely abolished the binding activity. The N-terminal limit of $IA^d$ binding region, can be identified as $I_{112}$, since its deletion from the N-terminus completely abolished all binding activity. The core region thus defined (Myo 112-117) (IHVLHS) strongly supports the validity of the alignments based on maximum structural similarity to Ova 327-332.

Next, the same set of overlapping Myo peptides were tested for their capacity to bind to $IE^d$. Two points arise from the results of this analysis, also shown in the Figure. First, although the same peptide region involved in binding to $IA^d$ appears to be involved in $IE^d$ binding, the C-terminal limit of the $IE^d$ binding region is $R_{118}$ (rather than $S_{117}$), since its removal from the C-terminus completely abolished the $IE^d$ interacting capacity. The N-terminal end of the $IE^d$ binding site appears to be centered on $I_{111}$ rather than $I_{112}$, since removal of this residue from the C-terminal end of the peptide series abolished the binding activity of the corresponding peptide. Thus, the critical binding segment for $IE^d$, appears to be contained within the sequence IIHVLHSR. This is in good agreement with the data reported by Livingstone et al. in Annual Reviews of Immunology 1987, "The Structure of T-Cell Epitopes", p. 477, Vol. 5, who defined the sequence IHVLHSR as the minimal common sequence recognized by a group of $IE^d$ restricted myoglobin specific T-cell hybrids.

Various modifications alterations to the above-described invention can of, course be ascertained by one skilled in the art. Accordingly, the present invention is not limited to the specific embodiments described above, but includes all those embodiments within the following claims.

We claim:

1. Method for determining a polypeptide which potentially generates an immunogenic response, comprising:

(i) contacting a first polypeptide which binds to an MHC molecule;

(ii) determining binding strength between said first polypeptide and said MHC molecule;

(III) contacting said MHC molecule with a second polypeptide which differs from said first polypeptide by having one amino acid less at one end as compared to said first polypeptide;

(iv) determining binding strength between said second polypeptide and said MHC molecule;

(v) continuing to contact said MHC molecule with a series of polypeptides, each member of said series of polypeptides differing from the polypeptide which preceded it by having one amino acid less at one end as compared to the polypeptide which preceded it and determining binding strength between the MHC molecule and each member of said series of polypeptides until a member of the series of polypeptides has a binding strength reduced by one half or more relative to the polypeptide which preceded it in the series, wherein said reduction in binding strength by one half or more indicates that the preceding polypeptide contains a critical binding segment;

(vi) contacting the polypeptide determined to contain said critical binding segment to a sample of T-cells; and (vii) measuring T-cell proliferation following the contacting in (vi), wherein a positive T-cell proliferation response is indicative of potential immunogenicity of said polypeptide.

2. Method for determining a polypeptide which binds to an MHC molecule comprising:

(i) contacting a first polypeptide which binds to an MHC molecule;

(ii) determining binding strength between said first polypeptide and said MHC molecule;

(iii) contacting said MHC molecule with a second polypeptide which differs from said first polypeptide by having one amino acid less at one end as compared to said first polypeptide;

(iv) determining binding strength between said second polypeptide and said MHC molecule;

(v) continuing to contact said MHC molecule with a series of polypeptides, each member of said series of polypeptides differing from the polypeptide which preceded it by having one amino acid less at one end as compared to the polypeptide which preceded it and determining binding strength between the MHC molecule and each member of said series of polypeptides until a member of the series of polypeptides has a binding strength reduced by one half or more relative to the polypeptide which preceded it in the series, wherein said reduction in binding strength by one half or more indicates that the preceding polypeptide contains a critical binding segment;

(vi) replacing at least one amino acid in the polypeptide determined to contain the critical binding segment;

(vii) determining the binding strength of the polypeptide having at least one amino acid replaced in (vi) to said MHC molecule; and (viii) comparing the binding strength in (vii) to that determined in, wherein a binding strength in (vii) equal to or greater than that in is indicative of a polypeptide which binds to said MHC molecule.

* * * * *